United States Patent
Vandendool

(10) Patent No.: US 12,011,384 B2
(45) Date of Patent: Jun. 18, 2024

(54) SELECTIVELY CLOSEABLE MEDICAL DEVICE FOR COLLECTING BODILY WASTE MATERIAL

(71) Applicant: Kellyann Vandendool, Ludington, MI (US)

(72) Inventor: Kellyann Vandendool, Ludington, MI (US)

(*) Notice: Subject to any disclaimer, the term of this patent is extended or adjusted under 35 U.S.C. 154(b) by 341 days.

(21) Appl. No.: 17/704,639

(22) Filed: Mar. 25, 2022

(65) Prior Publication Data

US 2022/0304845 A1    Sep. 29, 2022

Related U.S. Application Data

(60) Provisional application No. 63/166,111, filed on Mar. 25, 2021.

(51) Int. Cl.
| | | |
|---|---|---|
| *A61F 5/448* | (2006.01) | |
| *A61F 5/44* | (2006.01) | |
| *A61F 5/443* | (2006.01) | |

(52) U.S. Cl.
CPC .............. *A61F 5/448* (2013.01); *A61F 5/443* (2013.01); *A61F 5/4407* (2013.01)

(58) Field of Classification Search
CPC ......... A61F 5/448; A61F 5/445; A61F 5/4407
See application file for complete search history.

(56) References Cited

U.S. PATENT DOCUMENTS

| | | | | |
|---|---|---|---|---|
| 2,796,063 A * | 6/1957 | Smelser | ................... | A61F 5/448 604/342 |
| 3,089,493 A * | 5/1963 | Galindo | ................... | A61F 5/445 604/344 |
| 4,784,656 A * | 11/1988 | Christian | ................ | A61F 5/441 604/355 |
| 5,865,819 A * | 2/1999 | Cisko, Jr. | ................ | A61F 5/445 604/338 |

(Continued)

FOREIGN PATENT DOCUMENTS

| | | |
|---|---|---|
| EP | 0598625 B1 | 1/1999 |
| WO | WO-2003/101353 A2 | 12/2003 |
| WO | WO-2007/085803 | 8/2007 |

OTHER PUBLICATIONS

"Premier One-Piece High Output Ostomy Pouch—Flat Extend Barrier," Hollister Incorporated, retrieved from the Internet Dec. 9, 2020, https://www.hollister.com/en/products/ostomy-care-products/one-piece-pouching-systems/high-output-pouches/premier-one-piece-high-output-ostomy-pouch-_%C2%A0flat-flextend-barrier.

*Primary Examiner* — Guy K Townsend
(74) *Attorney, Agent, or Firm* — MARSHALL, GERSTEIN & BORUN LLP

(57) ABSTRACT

A medical device for use in collecting bodily waste material from a patient. The medical device includes a single pouch having a first side, a second side opposite the first side, and a waste receptacle defined between the first side and the second side, the waste receptacle adapted to hold the bodily waste material. The medical device also includes a ring non-removably coupled to the single pouch. The ring is (Continued)

reconfigurable between a first configuration, in which the ring is adapted to be attached to an orifice of the patient and defines an aperture that permits access to the waste receptacle, thereby fluidly connecting the waste receptacle to the orifice of the patient, and a second configuration, in which the ring prevents access to the waste receptacle.

18 Claims, 4 Drawing Sheets

(56) References Cited

U.S. PATENT DOCUMENTS

| | | | |
|---|---|---|---|
| 8,105,298 B2 * | 1/2012 | Mullejans | A61F 5/448 604/338 |
| 8,343,121 B2 * | 1/2013 | Cramer | A61F 5/445 604/344 |
| 8,740,832 B2 * | 6/2014 | Smith | A61F 5/445 604/8 |
| 9,498,372 B2 * | 11/2016 | Fattman | A61F 5/448 |
| 9,532,609 B2 * | 1/2017 | Stevenson | A41D 13/012 |
| 9,795,501 B2 * | 10/2017 | Nassopoulos | A61F 5/445 |
| 10,022,260 B2 * | 7/2018 | Richmann | A61F 5/4407 |
| 11,154,415 B2 * | 10/2021 | Johnson | A61F 5/4404 |
| 11,590,016 B1 * | 2/2023 | Kayal | A61F 5/443 |
| 2004/0059306 A1 * | 3/2004 | Tsal | A61F 5/4404 604/332 |
| 2010/0114045 A1 * | 5/2010 | Cramer | A61F 5/445 604/338 |
| 2011/0238024 A1 * | 9/2011 | Smith | A61F 5/445 604/336 |
| 2014/0309603 A1 * | 10/2014 | De Weert | A61F 5/445 156/308.2 |
| 2015/0320584 A1 * | 11/2015 | Kralovec | G10K 11/17857 604/337 |
| 2018/0360645 A1 * | 12/2018 | Fattman | A61F 5/443 |
| 2022/0241104 A1 * | 8/2022 | Knoedler | A61F 5/443 |
| 2022/0304845 A1 * | 9/2022 | Vandendool | A61F 5/448 |

* cited by examiner

SELECTIVELY CLOSEABLE MEDICAL DEVICE FOR COLLECTING BODILY WASTE MATERIAL

FIELD OF THE DISCLOSURE

The present disclosure generally relates to a medical device and, more particularly, to a medical device for collecting bodily waste material that is selectively closeable to prevent spillage of the collected bodily waste material when it is necessary to detach or transport the medical device.

BACKGROUND

Medical devices for collecting bodily waste from ostomy, colostomy, ileostomy, and urostomy patients are well known. FIG. 1 illustrates an example of such a medical device, in the form of a conventional ostomy bag 100. The conventional ostomy bag 100 illustrated in FIG. 1 has a first end 104 and a second end 108 opposite the first end 104. The first end 104 is open but can be clipped (e.g., by a sealing clip, not shown) or folded closed, while the second end 108 is also open and is surrounded by a first plastic ring 112. The ostomy bag 100 is attachable to an ostomy site (not shown) of a patient by fitting the first plastic ring 112 onto a wafer (also not shown) which has a second plastic ring that mates with the first plastic ring 112 and an adhesive bandage directly attached to the patient over the ostomy site. When the first plastic ring 112 mates with the second plastic ring of the wafer, the bodily waste from the patient can flow into and be collected by the ostomy bag 100 via the wafer and the first plastic ring 112. Meanwhile, the ostomy bag 100 can be emptied or irrigated via the first end 104. When desired, the ostomy bag 100 can be detached from the ostomy site by removing the first plastic ring 112 from the wafer (and more particularly the second plastic ring of the wafer). However, when it is necessary to detach the ostomy bag 100 from the ostomy site, care must be used to ensure that bodily waste does not spill out via the open first end 104. Care must also be used to ensure that bodily waste does not spill out via the open first end 104 after detachment and while the ostomy bag 100 is being transported from the ostomy site to, for example, waste.

SUMMARY

A medical device for use in collecting bodily waste material from a patient. The medical device includes a single pouch having a first side, a second side opposite the first side, and a waste receptacle defined between the first side and the second side, the waste receptacle adapted to hold the bodily waste material. The medical device also includes a ring non-removably coupled to the single pouch. The ring is reconfigurable between a first configuration, in which the ring is adapted to be attached to an orifice of the patient and defines an aperture that permits access to the waste receptacle, thereby fluidly connecting the waste receptacle to the orifice of the patient, and a second configuration, in which the ring prevents access to the waste receptacle.

BRIEF DESCRIPTION OF THE DRAWINGS

The features of this disclosure which are believed to be novel are set forth with particularity in the appended claims. The present disclosure may be best understood by reference to the following description taken in conjunction with the accompanying drawings, in which like reference numerals identify like elements in the several figures, in which:

DETAILED DESCRIPTION

The present disclosure is directed to a medical device that aims to solve the above-discussed and other problems with the conventional medical device 100 and other known medical devices. More particularly, the present disclosure is directed to a medical device that is attachable to an orifice (e.g., a colostomy site, an ostomy site, or other opening in the body) of a patient to collect bodily waste material from the orifice but is easily and selectively closeable to prevent spillage of the bodily waste material when it is necessary to remove the medical device from the wound site and transport the medical device from the orifice to, for example, waste. To this end, the medical device includes a ring that is easily reconfigurable (e.g., foldable) between a first configuration, in which the ring defines an aperture that permits access to an interior of the medical device, and a second configuration, in which the ring closes (i.e., prevents access to) the interior of the medical device. When it is necessary to collect bodily waste material from the patient, the ring can be placed in the first configuration and the medical device attached to the orifice of the patient. However, the ring can be moved from the first configuration to the second configuration when it is necessary to remove the medical device from the orifice of the patient, thereby ensuring that any collected bodily waste material is securely retained within the medical device after the medical device has been detached from the orifice of the patient.

Figure 1:
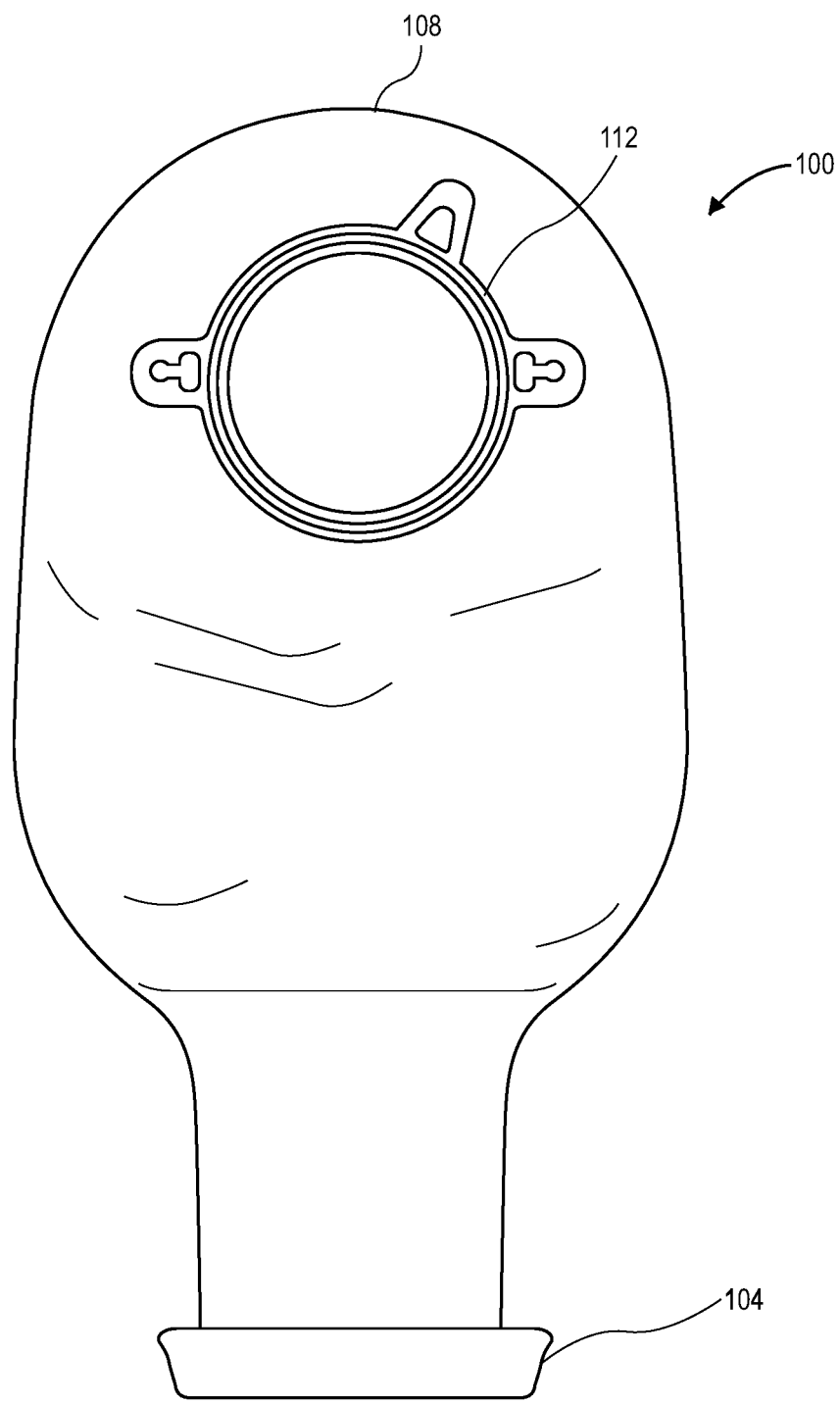
FIG. 1 illustrates an example of a conventional medical device for collecting bodily waste from a patient.
Figure 2:
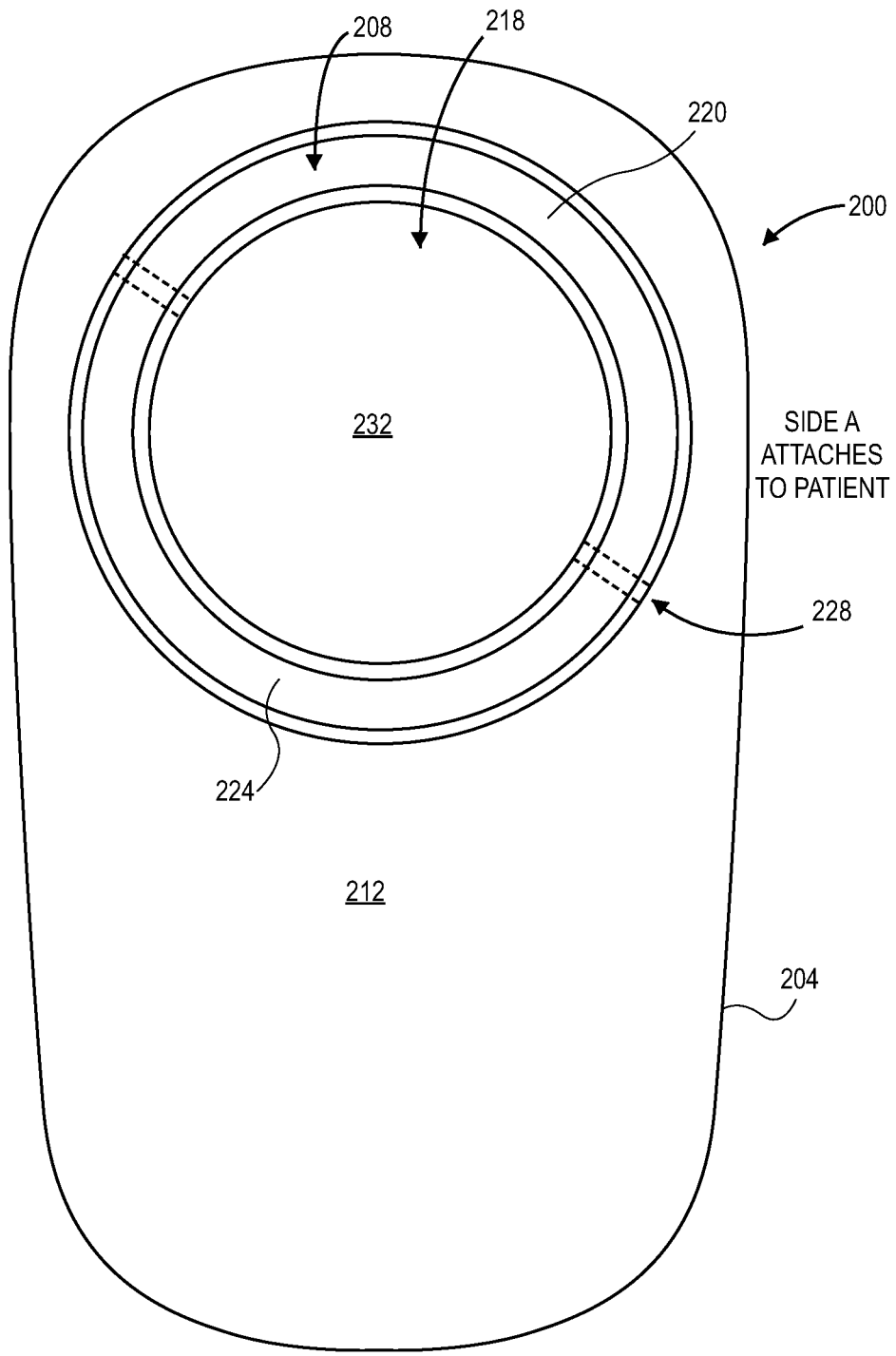
FIG. 2 is a front view of one example of a medical device constructed in accordance with the teachings of the present disclosure, the medical device having a ring that is in a first configuration.
Figure 3:
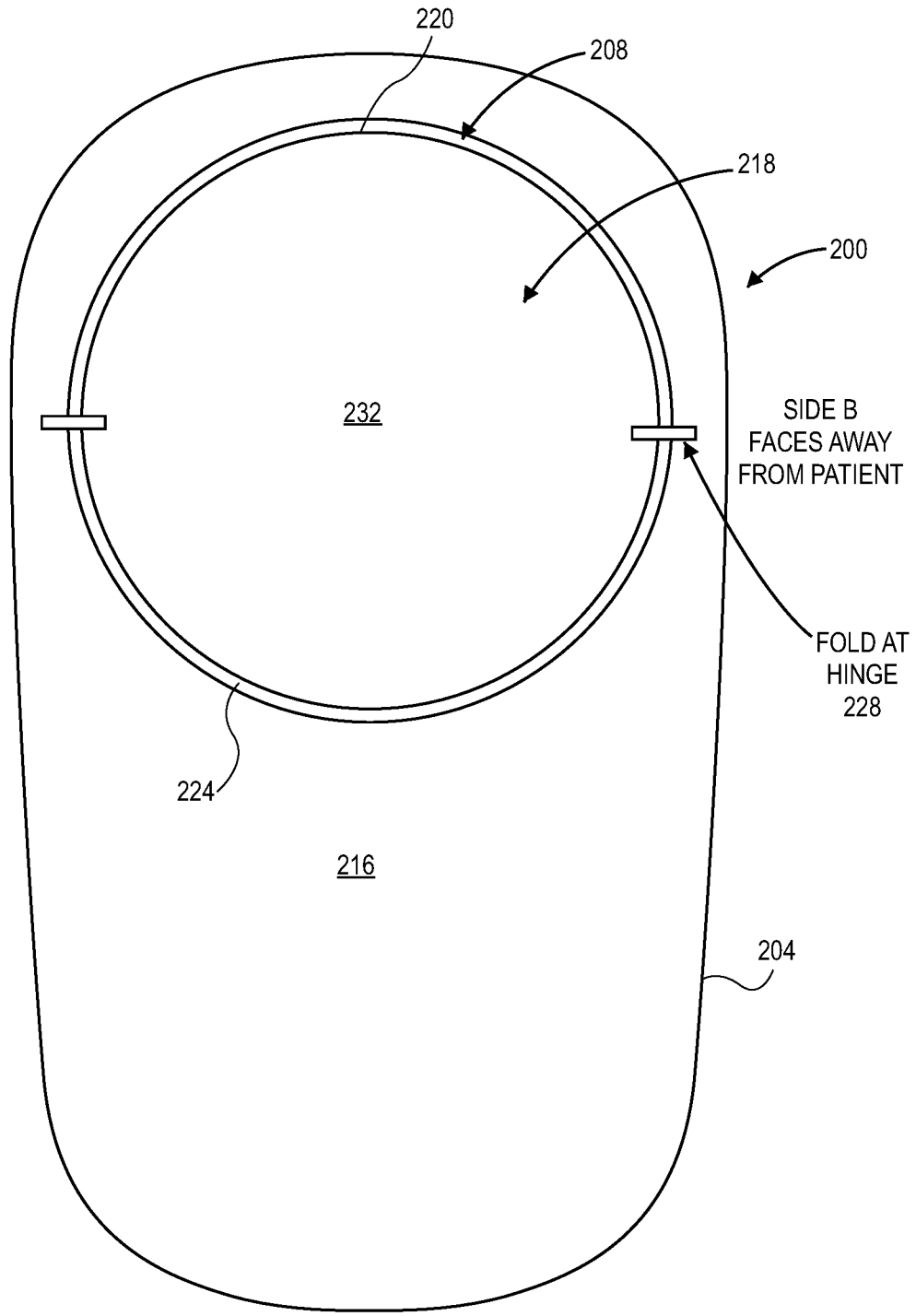
FIG. 3 is a rear view of FIG. 2.
Figure 4:
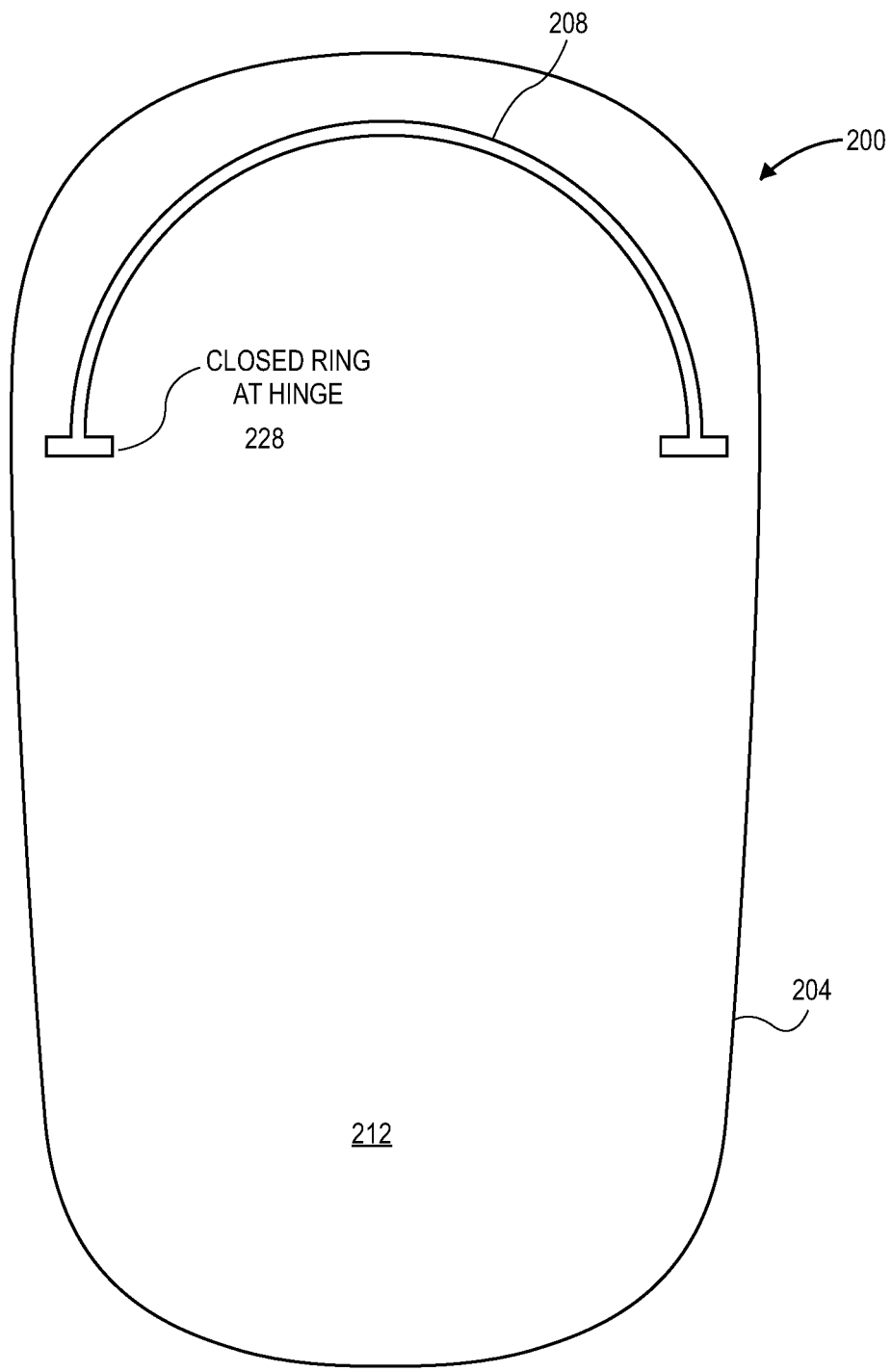
FIG. 4 is similar to FIG. 3 but shows the ring in a second configuration different from the first configuration.

FIGS. 2-4 illustrate one example of a medical device 200 that is constructed in accordance with the teachings of the present disclosure and can be used instead of the conventional medical device 100. In this example, the medical device 200 takes the form of an ostomy bag for collecting bodily waste material from an ostomy site (not shown) of a patient. In other examples, however, the medical device 200 can instead take the form of a colostomy bag, an ileostomy bag, an urostomy bag, or another type of bag for collecting bodily waste material from another orifice (e.g., an ileostomy site, an urostomy site, or other opening) of the patient.

The medical device 200 generally includes a single pouch 204 formed of one or known materials suitable for holding bodily waste material. For example, the single pouch 204 can be made of a tough, flexible, transparent waterproof material such as polyvinyl dichloride, ethylene vinyl alcohol, related materials, and combinations thereof. The single pouch 204 has a first side 212, a second side 216 opposite the first side 212, and a waste receptacle 218 defined between the first side 212 and the second side 216. When the medical device 200 is attached to the ostomy site of the patient, the waste receptacle 218 holds bodily waste material collected from the ostomy site.

The medical device 200 also generally includes a ring 208 coupled to the single pouch 204. In this example, the ring 208 is integrally formed with the first side 212 of the single pouch 204, such that the ring 208 is fixedly or non-removably coupled to the first side 212 of the single pouch 204. In other examples, however, the ring 208 can be coupled to the second side 216 of the single pouch 204 or coupled to the single pouch 204 in a different manner. In any event, the ring 208 in this example is a foldable or flexible ring that includes a first portion 220 and a second portion 224 movably connected to the first portion 220 via a living hinge 228 connecting the first portion 220 and the second portion 224. In this example, the first portion 220 and the second portion 224 are substantially (if not entirely) identical, with each of the first portion 220 and the second portion 224 having a substantially identical semi-circular shape. In other examples, however, the first portion 220 and/or the second portion 224 can have a different shape than illustrated (or than one another).

The ring 208 is reconfigurable between a first configuration, shown in FIGS. 2 and 3, and a second configuration, shown in FIG. 4. As illustrated in FIGS. 2 and 3, when the ring 208 is in the first configuration, the first portion 220 and the second portion 224 are aligned with one another such that the first portion 220 and the second portion 224 are substantially (if not entirely) coaxial with one another. In turn, the ring 208 defines an aperture 232, which in this example is circular, between the first portion 220 and the second portion 224. As such, the ring 208 is adapted to be attached to the ostomy site of the patient, with the aperture 232 permitting access to the waste receptacle 218 and fluidly connecting the ostomy site to the waste receptacle 218. In some examples, the ring 208 is adapted to be removably attached to the ostomy site via a wafer (not shown) attached to the ostomy site. In one example, the wafer can be integrally formed with the ring 208 and the wafer and the ring 208 can collectively be attached to the ostomy site. In any event, when the ring 208 is attached to the ostomy site, bodily waste material from the patient can in turn flow from the patient to the medical device 200 via the aperture 232. Meanwhile, as illustrated in FIG. 4, when the ring 208 is in the second configuration, the second portion 224 sealingly engages and substantially (if not entirely) covers the first portion 220 (and vice-versa). This, in turn, closes the aperture 232 (and the medical device 200 more generally), such that access to the waste receptacle 218 is no longer permitted.

Generally speaking, the ring 208 is positioned in the first configuration when it is desired use the medical device 200 to collect bodily waste material from the patient. Conversely, when it is necessary to remove the medical device 200 (because, for example, the waste receptacle 218 comprises a specified amount, e.g., is full or substantially full, of the bodily waste material), and after the medical device 200 has been detached from the patient, the ring 208 can be moved to the second configuration, either immediately after detachment or sometime thereafter. In this example, the ring 208 is movable between the first and second configurations by manipulating (e.g., folding) the first portion 220 relative to the second portion 224 (or vice versa) via the living hinge 228. Manipulation of the first portion 220 relative to the second portion 224 (or vice-versa) in this manner will typically be performed by a medical professional (e.g., doctor, nurse) assisting the patient, though it is possible that it may instead be performed by the patient himself/herself. In any event, movement of the ring 208 from the first configuration to the second configuration closes the medical device 200, thereby sealing the bodily waste material within the medical device 200 and preventing the bodily waste material from spilling out of the medical device 200. Thus, the medical device 200 can, for example, be transported without concern that the bodily waste material will undesirably be evacuated from the medical device during that transport.

Those skilled in the art will recognize that a wide variety of modifications, alterations, and combinations can be made with respect to the above described embodiments without departing from the scope of the disclosure, and that such modifications, alterations, and combinations are to be viewed as being within the ambit of the inventive concept.

The invention claimed is:

1. A medical device for use in collecting bodily waste material from a patient, the medical device comprising:
a single pouch having a first side, a second side opposite the first side, and a waste receptacle defined between the first side and the second side, the waste receptacle adapted to hold the bodily waste material;
a ring non-removably coupled to the single pouch, the ring reconfigurable between a first configuration, in which the ring is adapted to be attached to an orifice of the patient and defines an aperture that permits access to the waste receptacle, thereby fluidly connecting the waste receptacle to the orifice of the patient, and a second configuration, in which the ring prevents access to the waste receptacle.

2. The medical device of claim 1, wherein the ring is adapted to be removably attached to the orifice of the patient when the ring is in the first configuration.

3. The medical device of claim 1, further comprising a wafer configured to be removably coupled to the ring when the ring is in the first configuration.

4. The medical device of claim 1, wherein the ring comprises a first portion and a second portion movably connected to the first portion via a hinge, and wherein the hinge facilitates movement of the ring between the first configuration and the second configuration.

5. The medical device of claim 4, wherein the hinge is non-removably coupled to the second side of the single pouch.

6. The medical device of claim 4, wherein the first portion is semi-circular and the second portion is semi-circular.

7. The medical device of claim 4, wherein the second portion is substantially identical to the first portion.

8. The medical device of claim 1, wherein the ring is foldable to move the ring from the first configuration to the second configuration.

9. A medical device for use in collecting bodily waste material from a patient, the medical device comprising:
a single pouch having a first side, a second side opposite the first side, and a waste receptacle defined between the first side and the second side, the waste receptacle adapted to hold the bodily waste material;
a ring carried on the single pouch and comprising a first portion and a second portion movably connected to the first portion via a hinge, the ring being reconfigurable via the hinge between a first configuration, in which the second portion is aligned with the first ring portion, thereby defining an aperture that permits access to the waste receptacle and fluidly connecting the waste receptacle to an orifice of the patient when the ring is attached to the orifice of the patient, and a second configuration, in which the second portion substantially covers the first portion, thereby closing the aperture and preventing access to the waste receptacle.

10. The medical device of claim 9, wherein the ring is fixedly coupled to the single pouch.

11. The medical device of claim 10, wherein the ring is integrally formed with the single pouch.

12. The medical device of claim 9, wherein when the ring is in the first configuration, the second portion is coaxial with the first portion.

13. The medical device of claim 9, wherein the ring is adapted to be removably attached to the orifice of the patient when the ring is in the first configuration.

14. The medical device of claim 9, further comprising a wafer configured to be removably coupled to the ring.

15. The medical device of claim 9, wherein the hinge is partially fixedly coupled to the single pouch.

16. The medical device of claim 9, wherein the first portion is semi-circular and the second portion is semi-circular.

17. The medical device of claim 9, wherein the second portion is substantially identical to the first portion.

18. A method of collecting bodily waste material from a patient while preventing spillage, the method comprising:

providing a medical device comprising a single pouch and a ring non-removably coupled to the single pouch, the single pouch comprising a first side, a second side opposite the first side, and a waste receptable defined between the first side and the second side, wherein the ring is reconfigurable between a first configuration, in which the ring defines an aperture that permits access to the waste receptacle, and a second configuration, in which the ring prevents access to the waste receptacle;

when the ring is in the first configuration, attaching the medical device to the patient by attaching the ring to an orifice of the patient such that the bodily waste material is flowable from the orifice of the patient to the waste receptacle via the aperture; and when the waste receptacle comprises a specified amount of the bodily waste material, detaching the medical device from the patient by detaching the ring from the orifice of the patient, and moving the ring from the first configuration to the second configuration, thereby closing the aperture.

\* \* \* \* \*